United States Patent [19]

Murata et al.

[11] Patent Number: 5,084,557
[45] Date of Patent: Jan. 28, 1992

[54] DIAMINO COMPOUNDS AND LIQUID CRYSTAL ALIGNING FILMS

[75] Inventors: Shizuo Murata; Naoyoshi Emoto, both of Ichihara; Kenji Furukawa, Yokosuka; Kouichi Kunimune, Ichihara; Ryuji Kobayashi, Kawasaki; Masami Tanaka, Ichihara, all of Japan

[73] Assignee: Chisso Corporation, Osaka, Japan

[21] Appl. No.: 371,813

[22] Filed: Jun. 27, 1989

Related U.S. Application Data

[62] Division of Ser. No. 165,506, Mar. 8, 1988, Pat. No. 4,864,008.

[30] Foreign Application Priority Data

Mar. 9, 1987 [JP] Japan .................................. 62-53778
Jul. 22, 1987 [JP] Japan ................................ 62-182872
Jul. 22, 1987 [JP] Japan ................................ 62-182873

[51] Int. Cl.⁵ .................... C08G 69/26; C09K 19/00
[52] U.S. Cl. .................... 528/353; 528/125; 528/126; 528/128; 528/170; 528/172; 528/176; 528/183; 528/185; 528/187; 528/188; 528/220; 528/229; 528/350; 428/1; 428/473.5; 252/174.24; 359/75
[58] Field of Search ............... 528/353, 350, 125, 126, 528/128, 176, 170, 172, 183, 185, 220, 229, 187–188; 428/1, 473.5; 350/340, 341, 350 R; 252/174.24; 359/75

[56] References Cited

U.S. PATENT DOCUMENTS 4,316,844 2/1982 Waitkus et al. .................. 528/185
4,696,994 9/1987 Nakajima et al. ................ 528/125
4,847,349 7/1989 Ohta et al. ....................... 528/125

FOREIGN PATENT DOCUMENTS 60-68275 10/1986 Japan .
61-240223 10/1986 Japan .

*Primary Examiner*—Maurice J. Welsh
*Assistant Examiner*—P. Hampton-Hightower
*Attorney, Agent, or Firm*—Fleit, Jacobson, Cohn, Price, Holman & Stern

[57] ABSTRACT

The present invention provides diamino compounds and liquid crystal aligning films comprising polyimides which are obtained from the said diamino compounds represented by the general formula:

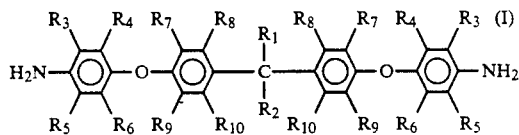

wherein $R_1$ indicates an alkyl group having 3 to 22 carbon atoms, $R_2$ indicates a hydrogen atom or an alkyl group having 1 to 22 carbon atoms, and $R_3$–$R_{10}$ indicate a hydrogen atom or a methyl group, respectively.

The liquid crystal aligning films are useful for STN mode display cells in realizing a high pretilt angle.

9 Claims, 15 Drawing Sheets

DIAMINO COMPOUNDS AND LIQUID CRYSTAL ALIGNING FILMS

This is a divisional of application Ser. No. 165,506, filed Mar. 8, 1988, now U.S. Pat. No. 4,864,008, issued July 11, 1989.

BACKGROUND OF THE INVENTION

The present invention relates to diamino compounds which are useful for material monomers of high-molecular compounds such as polyimides, polyamides, epoxy resins and the like, crosslinking agents and modifiers, and to liquid crystal aligning films comprising polyimides which are obtained from the diamino compounds.

The main current of liquid crystal display elements which are used in conventional clocks, watches and electronic calculators is a twist nematic (abbreviated as TN hereinafter) mode having a structure in which molecular alignment of nematic liquid crystals is twisted at an angle of 90° on the surface of a couple of upper and lower electrode substrates.

However, this display mode is insufficient to obtain improved display in quality and size because it shows an indistinct contrast and a narrow viewing angle.

In recent years, a liquid crystal display element using supertwist nematic (abbreviated as STN hereinafter) mode in which the molecular alignment of nematic liquid crystals is twisted at angles of 180-270 degrees between the upper and lower electrode substrates has been developed, and then large panel liquid crystal elements having sufficient display quality are developing. Among these elements, in an element having a relatively narrow twist angle (twisted at 180-200 degrees), surface treatment on the electrode substrates is sufficiently conducted in the similar manner to those employed in conventional TN cells which are equipped with aligning films having surface alignment of pretilt angles (abbreviated as $\theta$ hereinafter) of five degrees and below. In the specification, the pretilt angle means the angle between the rod-shaped liquid crystal molecules and the substrate of the liquid crystal cell. In STN modes having twist angles of 200-270 degrees along with better display quality, surface alignment having higher pretilt angles ($10° < \theta \leq 30°$) must be used, and therefore liquid crystal display cells having the aligning films which satisfy these angles are required.

In polyimide aligning films which are currently available for the TN mode, the limit of pretilt angles of display cells produced on a technical scale is about five degrees.

Japanese Publication of Unexamined Patent Application No.61-240223 describes a liquid crystal display element which is equipped with liquid crystal aligning films produced from a polyimide resin.

The resin has a repeating unit represented by a formula:

wherein $R_1$ and $R_2$ indicate the same or different groups selected from a hydrogen atom, an alkyl group having one to four carbon atoms and $CF_3$, and $R_3$ and $R_4$ indicate the same or different groups selected from a hydrogen atom and an alkyl group having one to four carbon atoms. As materials for the polyimide resin, the only diamine represented by a formula:

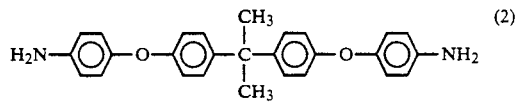

is exemplified.

However, the polyimide aligning films produced from the above diamine have a problem that high pretilt angles are unobtainable as shown in the comparative examples described hereinafter.

Furthermore, there are polyimide aligning films having high pretilt angles for the STN mode.

Problems of these films are stability and reproducibility of pretilt angles over the whole display surface of a cell substrate. In order to obtain the high pretilt angles definitely, the best method which is currently conducted is film formation by vacuum oblique evaporation of SiO and the like.

However, as the films are mass-produced by the vacuum evaporation, it is a costly process in its production unit.

As the result, it is desired earnestly to realize the aligning films having high pretilt angles by the surface treatment of rubbing organic films that is the same method as in the conventional surface treatment method which has been employed in the TN mode.

SUMMARY OF THE INVENTION

An object of the present invention is to provide diamino compounds which are materials of polyimide compounds for obtaining organic aligning films having excellent aligning properties and high pretilt angles.

Another object of the present invention is to provide liquid crystal aligning films which can offer high pretilt angles and excellent aligning properties of liquid crystals.

For achieving the above objects, a first feature of the present invention is a diamino compound represented by the general formula:

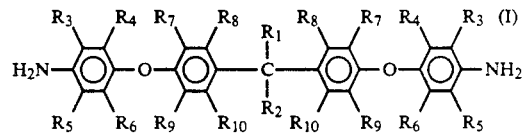

wherein $R_1$ indicates an alkyl group having 3 to 22 carbon atoms, $R_2$ indicates a hydrogen atom or an alkyl

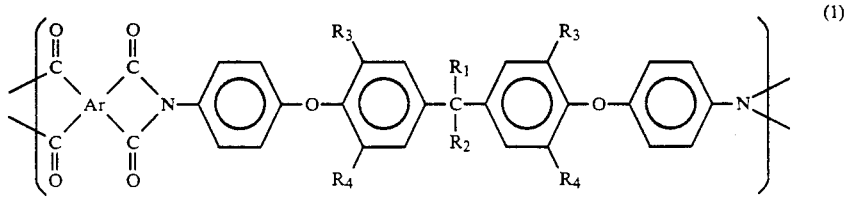

group having 1 to 22 carbon atoms, and $R_3$-$R_{10}$ indicate a hydrogen atom or a methyl group, respectively.

A second feature of the present invention is a liquid crystal aligning film which is characterized by containing a polymeric material of a polyimide type having a structure unit represented by the general formula:

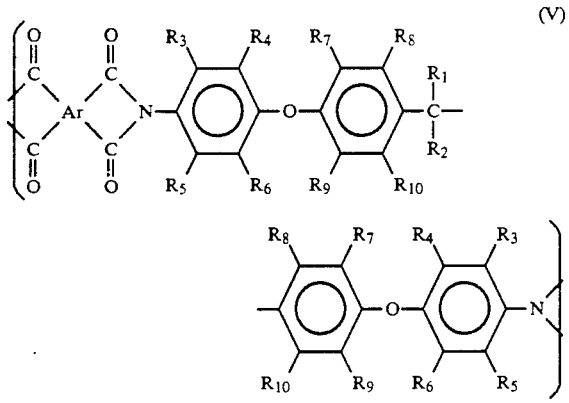

wherein $R_1$-$R_{10}$ indicate the same meaning of the formula (I), and Ar indicates an aromatic group of four valences. The polymer is obtained by using the diamino compound (I) as a raw material.

DETAILED DESCRIPTION OF THE PRESENT INVENTION

Figure 1:
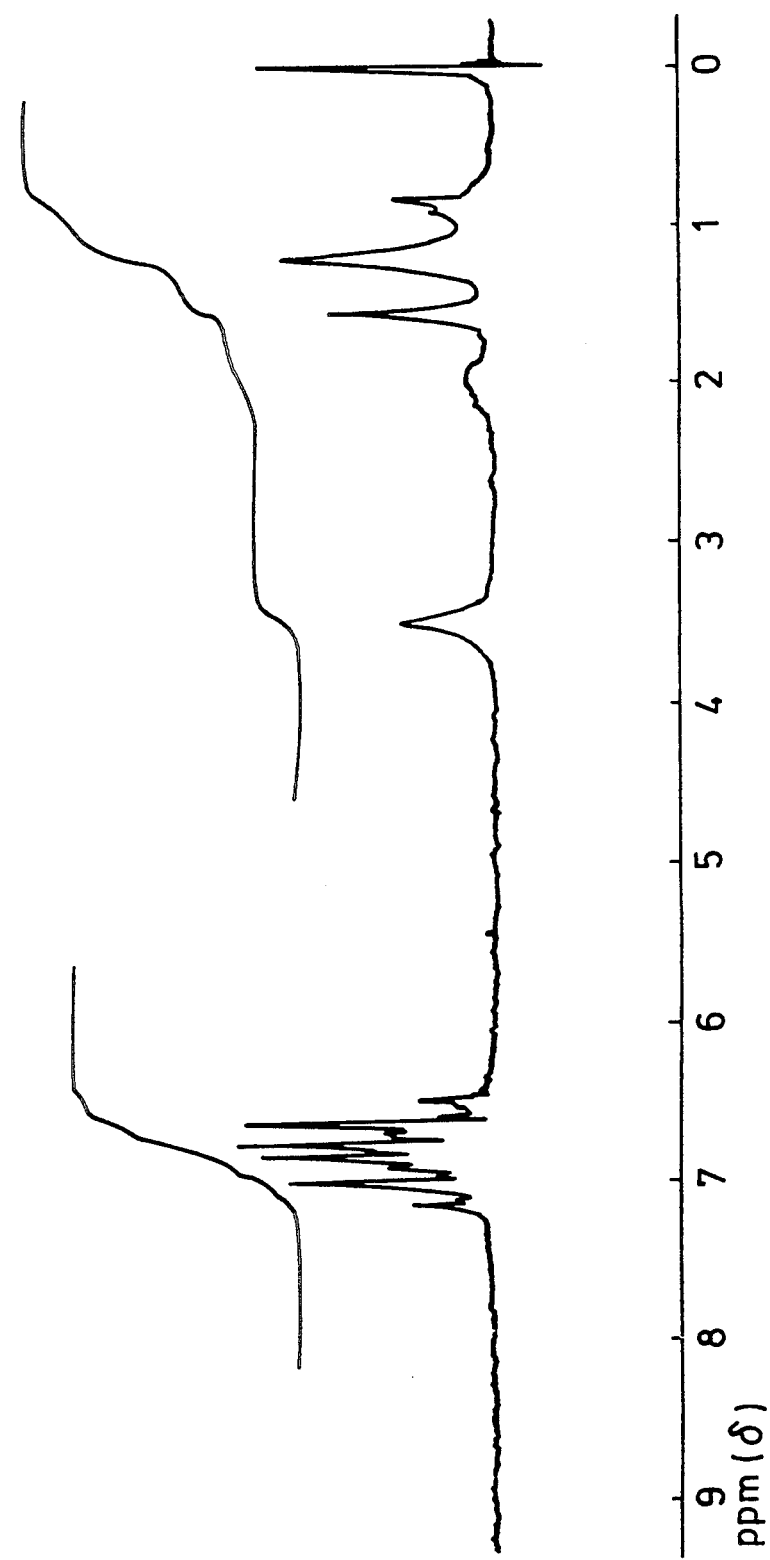
FIGS. 1 and 2 are $^1$H-NMR spectrum and IR spectrum of 2,2-bis[4-(4-aminophenoxy)phenyl]octane which is obtained in Example 1, respectively.

When the compounds of the present invention are used as raw materials of polyimides for liquid crystal aligning films, $R_2$ in the formula (I) is preferably an alkyl group. When $R_2$ is a methyl group or an ethyl group, $R_1$ is desirably a straight-chain alkyl group having 4 to 12 carbon atoms, more preferably, $R_1$ is a straight-chain alkyl group having 5 to 10 carbon atoms.

Diamino compounds of the present invention include for instance 2,2-bis[4-(4-aminophenoxy)phenyl]heptane, 2,2-bis[4-(4-aminophenoxy)phenyl]octane, 2,2-bis[4-(4-aminophenoxy)phenyl]nonane, 2,2-bis[4-(4-aminophenoxy)phenyl]decane, 2,2-bis[4-(4-aminophenoxy)phenyl]undecane, 2,2-bis[4-(4-aminophenoxy)phenyl]dodecane, 2,2-bis[4-(4-aminophenoxy)phenyl]hexane, 2,2-bis[4-(4-aminophenoxy)phenyl]pentane, 3,3-bis[4-(4-aminophenoxy)phenyl]heptane, 3,3-bis[4-(4-aminophenoxy)phenyl]octane, 3,3-bis[4-(4-aminophenoxy)phenyl]nonane, 3,3-bis[4-(4-aminophenoxy)phenyl]decane, 3,3-bis[4-(4-aminophenoxy)phenyl]undecane, 3,3-bis[4-(4-aminophenoxy)phenyl]dodecane, 3,3-bis[4-(4-aminophenoxy)phenyl]hexane, 3,3-bis[4-(4-aminophenoxy)phenyl]pentane, and the like.

When the sum of carbon numbers of the alkyl chains of $R_1$ and $R_2$ in the formula (I) is three or less, it is undesirable because the liquid crystal cells obtained by using the polyimide aligning films obtained can not exhibit wider tilt angles.

When the sum of carbon numbers of the alkyl chains of $R_1$ and $R_2$ is 25 or more, it is undesirable because the obtained polyimide films have low thermal stability.

The compounds of the present invention are mainly used as the raw materials or intermediates of the organic aligning films for the STN display cells. The compounds also can be used for production of high-molecular compounds such as other polyimides, polyamides and the like, and for modification thereof. The compounds also can be used for other objects such as epoxy crosslinkers.

The polyimide compounds prepared by using the diamino compounds of the present invention as one of the raw materials can realize the high pretilt angles which are necessary to the STN liquid crystal display elements by the conventional rubbing treatment. It is thought that the high tilt angles are derived from the long-chain alkyl groups of diamino compounds of the raw materials.

The compounds of the present invention are most preferably synthesized by the following reaction process which is summarized as an example.

Reaction process

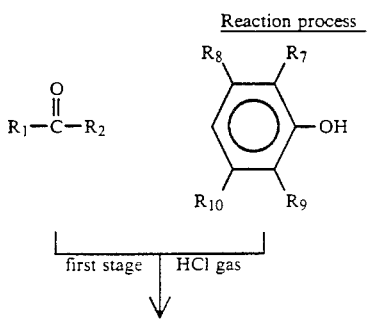

first stage | HCl gas

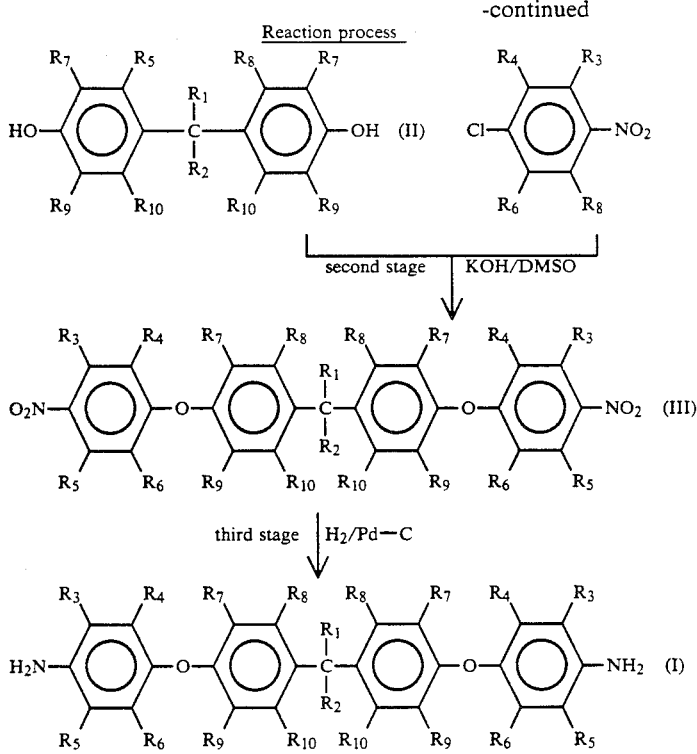

Reaction process second stage KOH/DMSO third stage H₂/Pd—C wherein $R_1$ indicates an alkyl group having 3 to 22 carbon atoms, $R_2$ indicates a hydrogen atom or an alkyl group having 1 to 22 carbon atoms, and $R_3$-$R_{10}$ indicate a hydrogen atom or an methyl group, respectively.

The production process is outlined hereinafter.

First stage A aliphatic alkanone or alkanal and phenol or its derivative (e.g. o-cresol, m-cresol, 2,6-dimethyl phenol) are reacted with hydrogen chloride gas in the absence of solvent or in a suitable solvent such as toluene or xylene, and compound (II) is obtained.

Second stage Compound (II) and p-chloronitrobenzene or its derivative (e.g. 5-chloro-2-nitrotoluene) are condensed with KOH or NaOH in a solvent of dimethyl sulfoxide (abbreviated as DMSO hereinafter), and compound (III) is obtained.

Third stage By hydrogen reduction of compound (III) in a suitable solvent such as toluene, xylene or benzene in the presence of palladium-carbon (abbreviated as Pd-C hereinafter) catalyst, compound (I) is obtained.

As shown in the above process, by appropriate selection of $R_1$, $R_2$ and $R_7$-$R_{10}$ in the first stage and $R_3$-$R_6$ in the second stage, all kinds of desired diamino compounds (I) can be prepared selectively.

Liquid crystal cells have aligning coatings of polyimides prepared from these diamino compounds. The pretilt angles of the cells are mainly influenced by the chain length of $R_1$ and $R_2$, and also by the rubbing process which is one of the main processes for producing the liquid crystal display elements. Pretilt angles may vary in a certain range with other factors such as a kind of liquid crystals employed, preparation condition of the aligning films, and the like. For these factors, the chain length of $R_1$ and $R_2$ of the diamino compounds of the present invention can be selected optionally.

The polyimides for liquid crystal aligning films of the present invention have imide bonds and these are insoluble in a general solvent. For providing homogeneous polyimide films on a substrate, preferably, a precursor polyamic acid which is obtained by common condensation of a tetracarboxylic dianhydride and a diamino compound is dissolved in a solvent such as N-methyl-2-pyrrolidone (NMP), dimethylacetamide (DMAc), dimethylformamide (DMF), dimethyl sulfoxide (DMSO). After the resulting solution is applied on the substrate by a method such as a brush method, a dipping method, a rotation coating method, a spray method, a printing method and the like, the substrate is heated at 100°-450° C., preferably 150°-300° C., according to the above preferable method, imide bonds of the polyimide are obtained by dehydration and ring closure of the precursor.

The above precursor polyamic acid for providing the polyimide is generally prepared by condensation between a tetracarboxylic dianhydride and a diamino compound.

The condensation is conducted under anhydrous conditions in a solvent such as N-methyl-2-pyrrolidone (NMP), dimethylacetamide (DMAc), dimethylformamide (DMF), dimethyl sulfoxide (DMSO), dimethyl sulfate, sulfolane, butyrolactone, cresol, phenol, a halogenated phenol, cyclohexanone, dioxane, tetrahydrofuran and the like, preferably N-methyl-2-pyrrolidone (NMP) at temperatures of 50° C. or lower. When the polyimide is soluble in a solvent, the precursor polymer may be reacted at high temperatures before coating it on the substrate as polyimide varnish.

The tetracarboxylic dianhydrides include for instance pyromellitic dianhydride, 3,3',4,4'-biphenyltetracarboxylic dianhydride, 2,2',3,3'-biphenyltetracarboxylic dianhydride, 2,3,3',4'-biphenyltetracarboxylic dianhydride, 3,3',4,4'-benzophenonetetracarboxylic dianhydride, 2,3,3',4'-benzophenonetetracarboxylic dianhydride, 2,2',3,3'-benzophenonetetracarboxylic dianhydride, bis(3,4-dicarboxyphenyl)ether dianhydride, bis(3,4-dicarboxyphenyl)sulfone dianhydride, 1,2,5,6-naphthalenetetracarboxylic dianhydride, 2,3,6,7-naphthalenetetracarboxylic dianhydride and the like.

To increase the adhesivity of the polyimide aligning films on the substrates, an aminosilicon compound or a diaminosilicon compound can be added to denature the polyimide. The aminosilicon compounds represented by the following formulas can be exemplified.

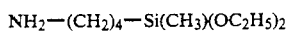

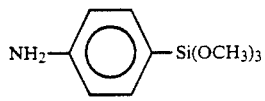

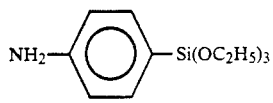

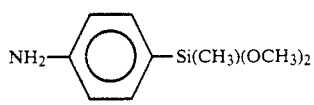

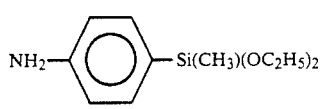

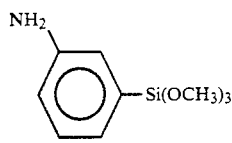

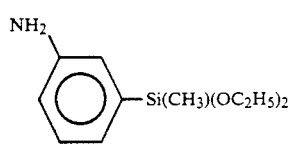

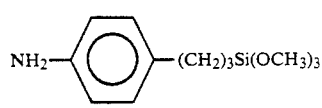

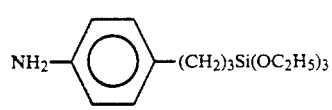

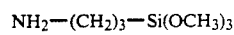

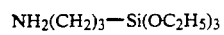

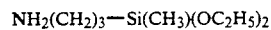

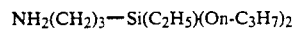

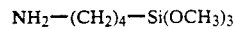

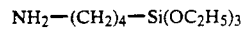

When these aminosilicon compounds are added to the polyimide type polymers which are used in the present invention, the contents of the compounds can be used so as to satisfy the range of the following relations.

$$1 \leq \frac{C}{A-B} \leq 2 \text{ and } 0.1 \leq \frac{C}{B+C}$$

wherein A, B and C show molar numbers of the tetracarboxlic dianhydrides, the diamino compounds represented by general formula (I) and the aminosilicon compounds, respectively.

The diaminosilicon compounds represented by the following formulas can be also exemplified.

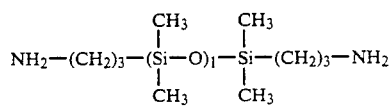

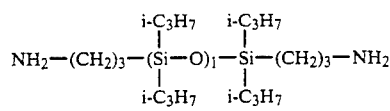

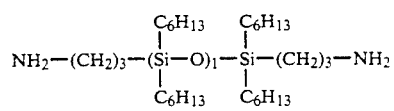

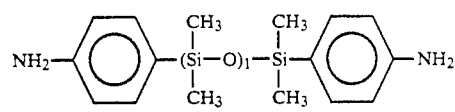

wherein l indicates an integral number of 0–4.

When the diaminosilicon compounds are added to the polyimides, the diaminosilicon compounds can be replaced by 50 mol % or less, preferably 30 mol % or less of the diamino compounds represented by the above formula (I).

The polyimides for the liquid crystal aligning films of the present invention can be denatured by adding other diamino compounds, such as aromatic diamino compounds, alicyclic diamino compounds and their derivatives.

The above diamino compounds are 4,4'-diaminophenylether, 4,4'-diaminodiphenylmethane, 4,4'-diaminodiphenyl sulfone, 4,4'-diaminodiphenyl sulfide, 4,4'-di(meta-aminophenoxy)diphenyl sulfone, 4,4'-di(-para-aminophenoxy)diphenyl sulfone, ortho-phenylenediamine, meta-phenylenediamine, para-phenylenediamine, benzidine, 2,2'-diaminobenzophenone, 4,4'-diaminobenzophenone, 4,4'-diaminodiphenyl-2,2'-propane, 1,5-diaminonaphthalene, 1,8-diaminonaphthalene and the like as aromatic diamino compounds, and alicyclic diamino compounds such as 1,4-diaminocyclohexane, etc.

These diamino compounds can be replaced by 50 mol % or less, preferably 30 mol % or less of the diamino compounds represented by the above formula (I).

When the adhesivity of the obtained polyimide type polymer coating to the substrate is not good, the surface of the substrate is previously treated with a silane coupling agent, and then the polyimide film is formed on the substrate.

The obtained film surface is then repeatedly rubbed in the same directions, and a liquid crystal aligning film is obtained.

The measurement of the pretilt angle θ is described hereinafter.

The polyimide films provided by the above method on the liquid crystal element substrates are repeatedly rubbed in the same directions for a certain times with a rubbing device such as a liquid crystal cell rubbing device made by Kyoei Semiconductor Company. The liquid crystal elements having thickness of about 10 μm are assembled by the resulting liquid crystal element substrates so as to obtain the elements oriented in parallel and anti parallel rubbing directions between the two substrates. A nematic liquid crystal, of which parallel dielectric constants ($\epsilon \parallel$) and perpendicular dielectric constants ($\epsilon \perp$) are known, is kept in the liquid crystal elements. Sufficiently lower voltage than threshold voltage is applied to the elements and the dielectric constants ($\epsilon$) are measured. According to the following equation, $\theta$ is determined.

$$\epsilon = \epsilon \parallel \sin^2\theta + \epsilon \perp \cos^2\theta \quad (3)$$

In this equation, the values $\epsilon \parallel$ and $\epsilon \perp$ are given by the application of sufficiently lower voltage than threshold voltage of Freedericksz transition with a homeotropic alignment cell and a homogeneous alignment cell, respectively.

DESCRIPTION OF THE PREFERRED EMBODIMENTS

The following examples illustrate the present invention more specifically, but these will not always be precise in practical applications.

EXAMPLE 1

1st stage

A thousand grammes of 2-octane and 1,468 g of phenol was mixed and vigorously stirred at room temperature during hydrochloric acid gas was blown.

The mixture was reacted for 48 hours and left for more 48 hours at room temperature.

Meantime, the viscosity of the reaction solution increased. At the conclusion of the reaction, 2,000 ml of toluene was added to the solution, the mixture was washed and hydrochloric acid was removed. After toluene was distilled away, the residue was distilled under reduced pressure to remove low boiling point fractions which mainly consisted of unreacted materials. 1,000 g of 2,2-bis(4-hydroxyphenyl)octane was obtained as a tarry product.

The obtained tarry material was recrystallized from an ethanol-heptane mixed solvent and light-brown crystals were obtained.

2nd stage

Fifty grammes of 2,2-bis(4-hydroxyphenyl)octane obtained by the first stage, 66.0 g of p-chloronitrobenzene and 28.2 g of KOH were mixed and dissolved in 500 ml of DMSO, and the mixture was stirred for about 60 hours at 100° C. After the reaction finished, the reaction mixture was cooled to room temperature, and added to a mixture of dilute hydrochloric acid and ice. The organic phase was extracted with toluene. The obtained toluene phase was washed with a dilute hydrochloric acid solution and then an aqueous alkaline solution. After the toluene phase was washed with water until the washed water became neutral, toluene was distilled away from the obtained solution. 84.2 g of oily yellow brown 2,2-bis[4-(4-nitrophenoxy) phenyl] octane was obtained.

3rd stage

After 84.2 g of 2,2-bis[4-(4-nitrophenoxy)phenyl]octane obtained by the second stage was dissolved in toluene, 5 g of Pd-C catalyst (5% quality, 55.9% moisture content) was added to the solution and stirred at 40° C. at ordinary pressure in contact with hydrogen gas. As the reaction proceeded, water release was observed. After absorption of hydrogen gas was stopped, the catalyst was filtered off, low boiling materials were distilled away and the products were concentrated. The concentrated products were dissolved in chloroform and isolated by column chromatography on silica gel. After the solvent was distilled off, 43.4 g of brownish glassy 2,2-bis [4-(4-aminophenoxy)phenyl]octane was obtained.

Figure 2:
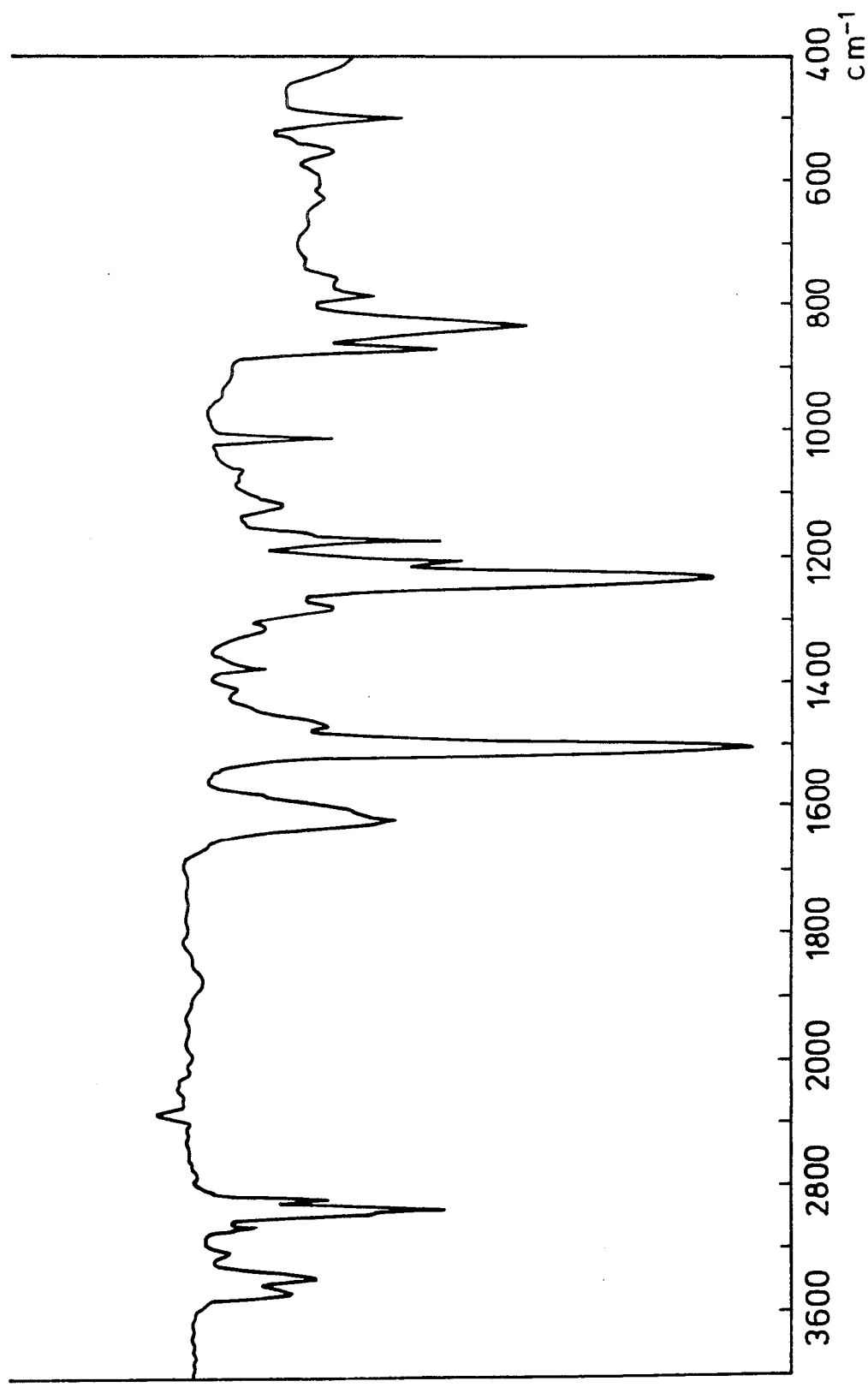

FIGS. 1 and 2 show a 60 MHz proton nuclear magnetic resonance (NMR) spectrum and an infrared (IR) spectrum of the obtained compound, respectively.

EXAMPLE 2

Conditions of operation were the same as described in Example 1, except the raw material 2-octanone was changed to 2-pentanone.

Figure 3:
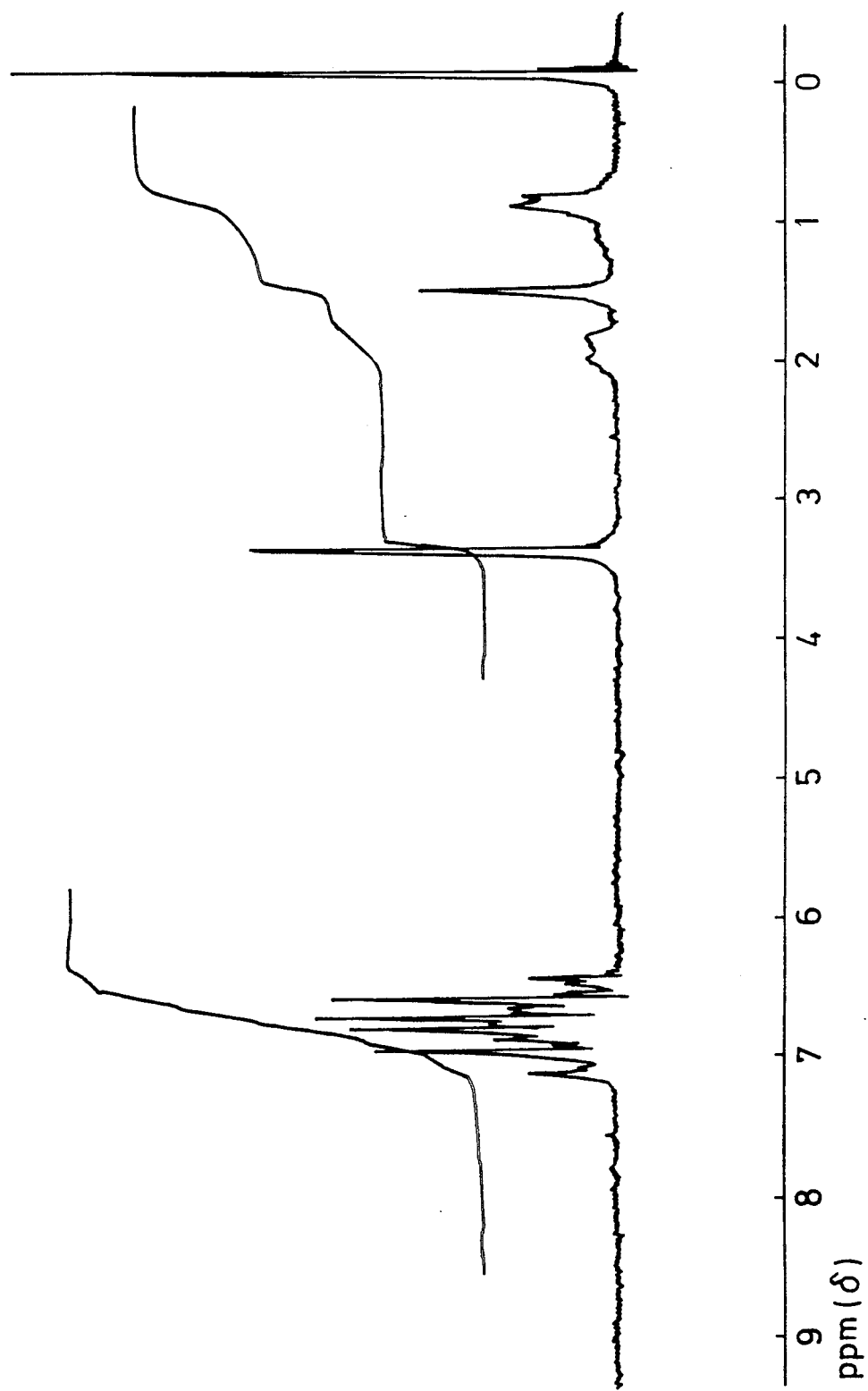
FIGS. 3, 5, 7, 9 and 11 are $^1$H-NMR spectra of diamino compounds which are shown in Examples 2-6, respectively.
Figure 4:
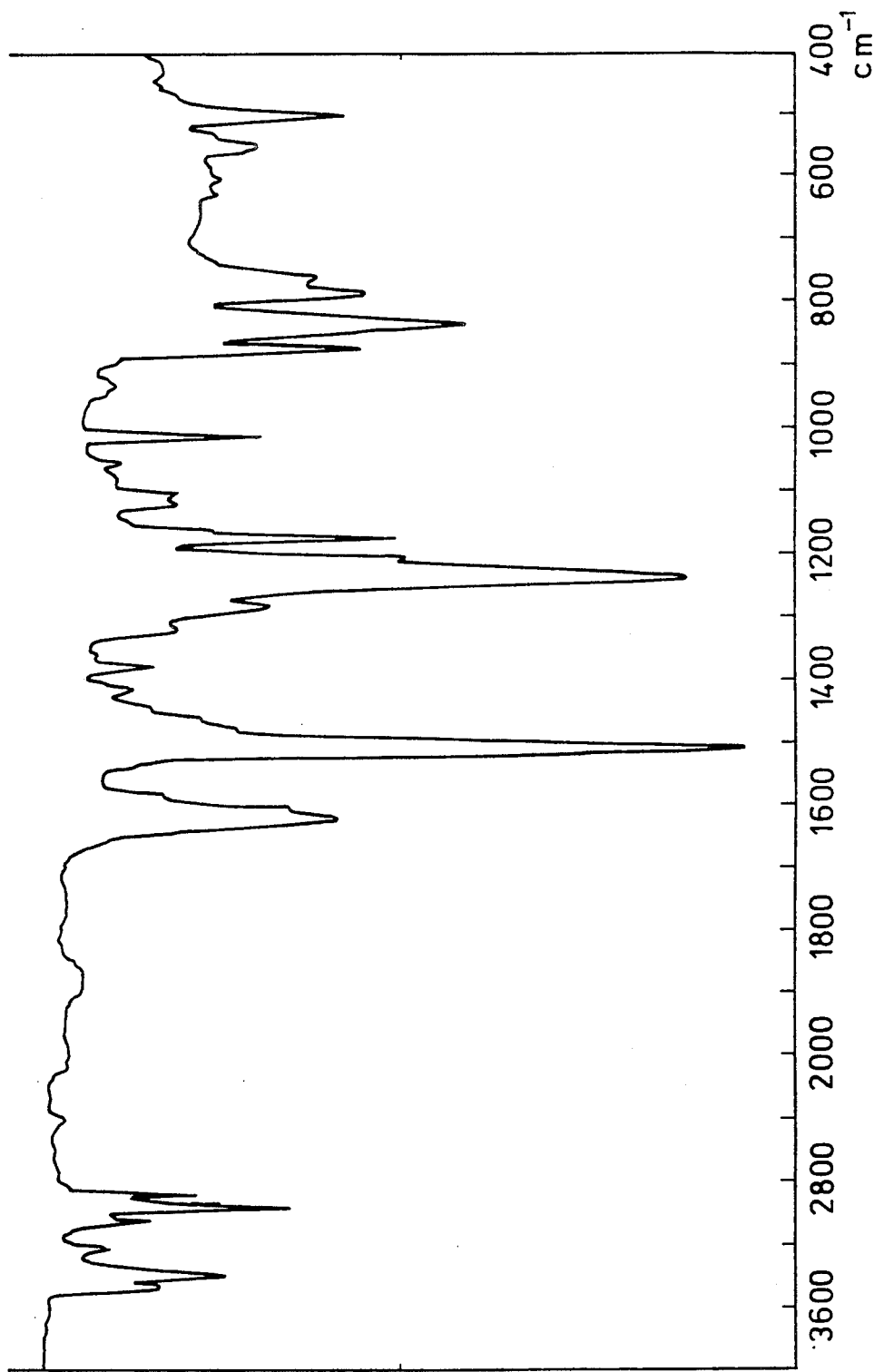
FIGS. 4, 6, 8, 10 and 12 are IR spectra of the diamino compounds, which are shown in Examples 2-6, respectively.
Figure 5:
Figure 6:
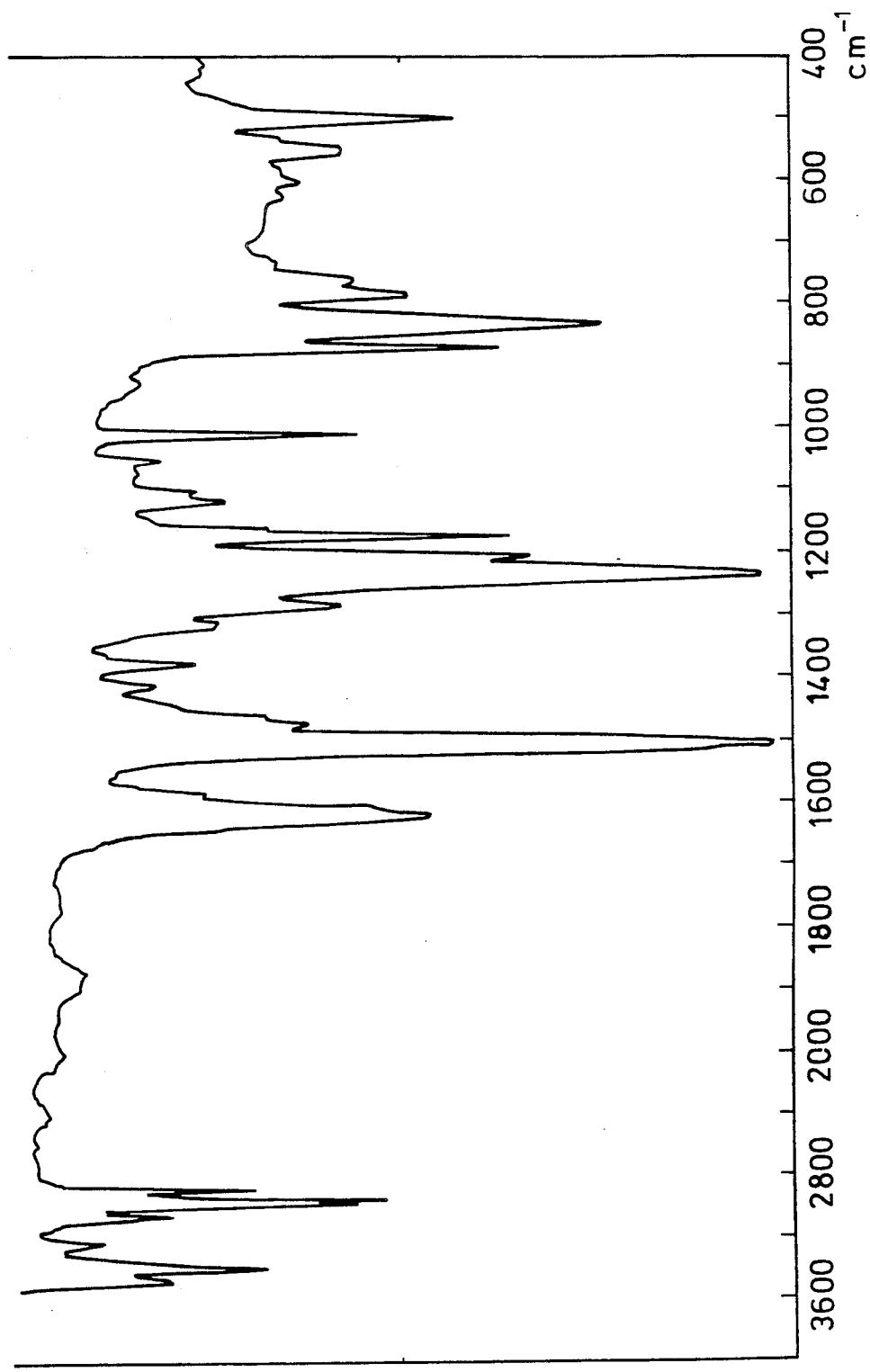
Figure 7:
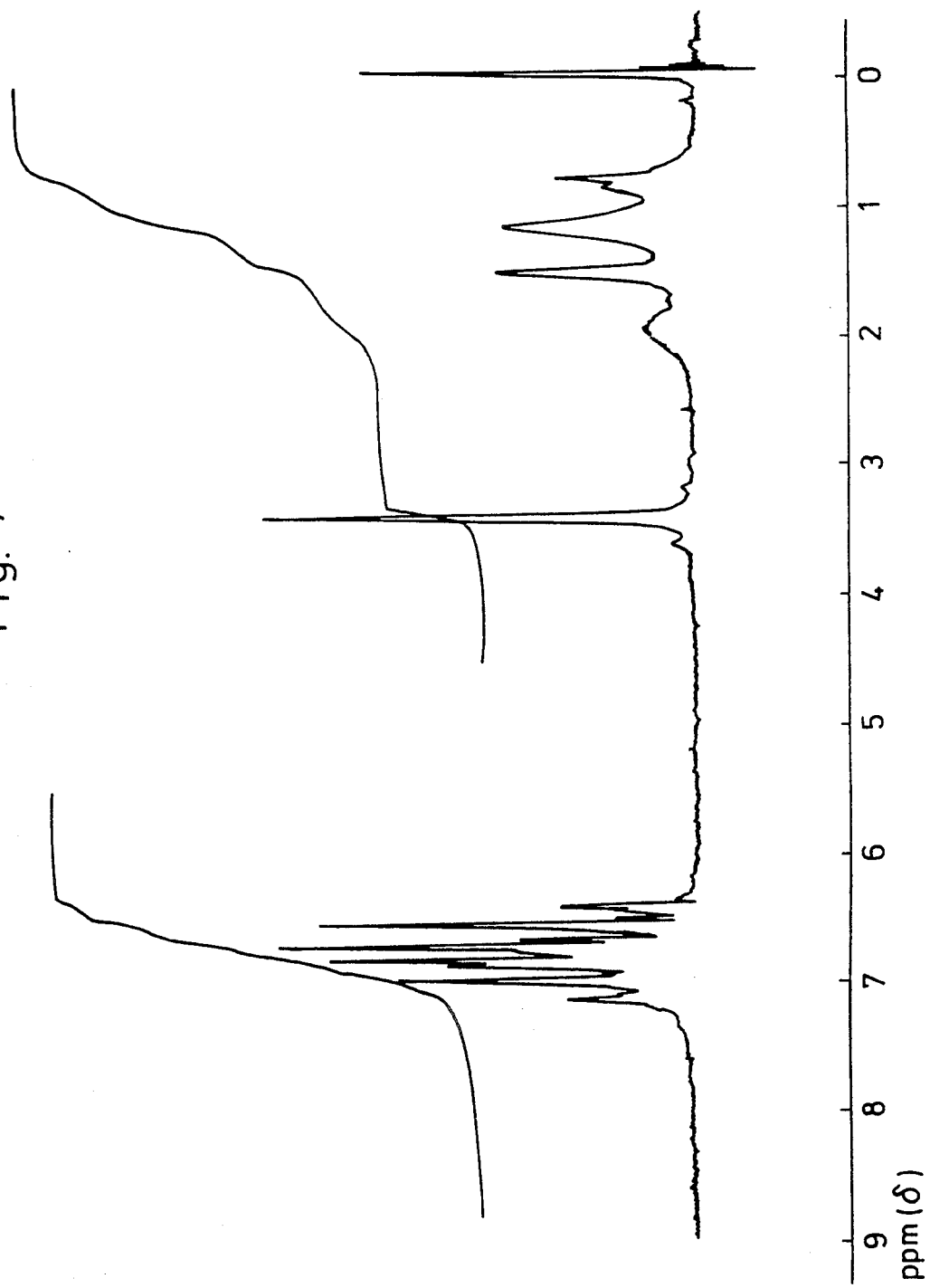
Figure 8:
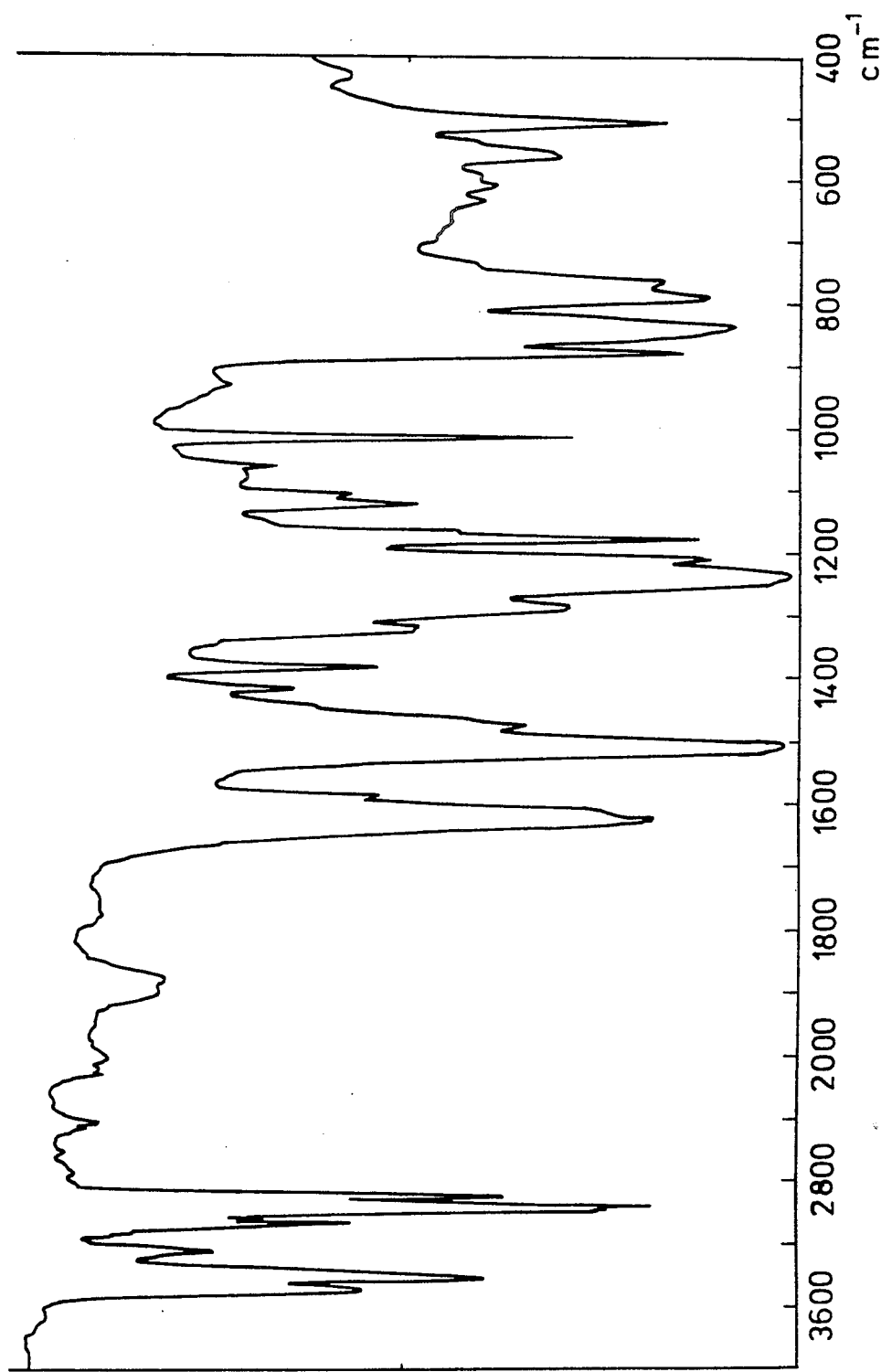
Figure 9:
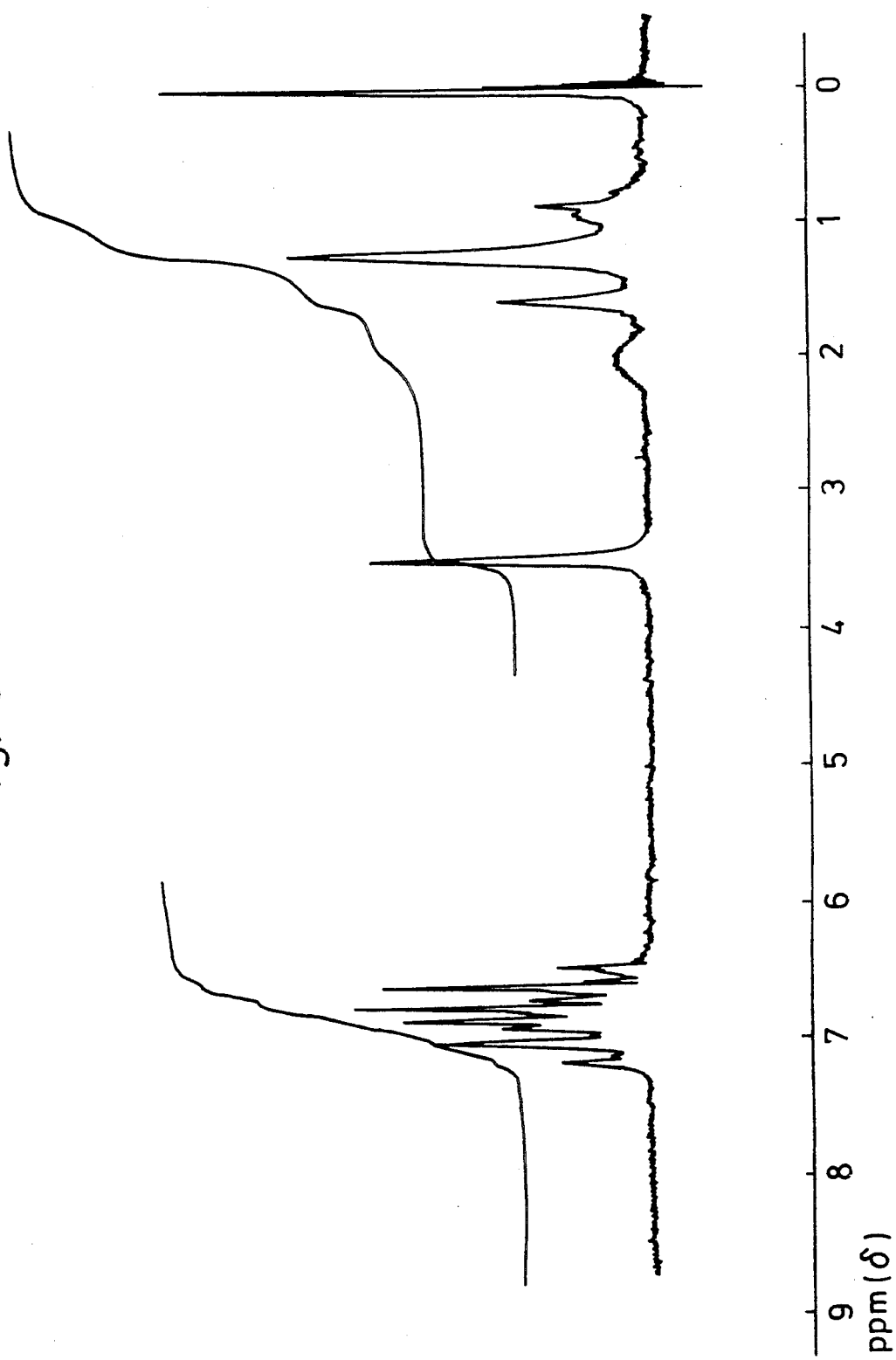
Figure 10:
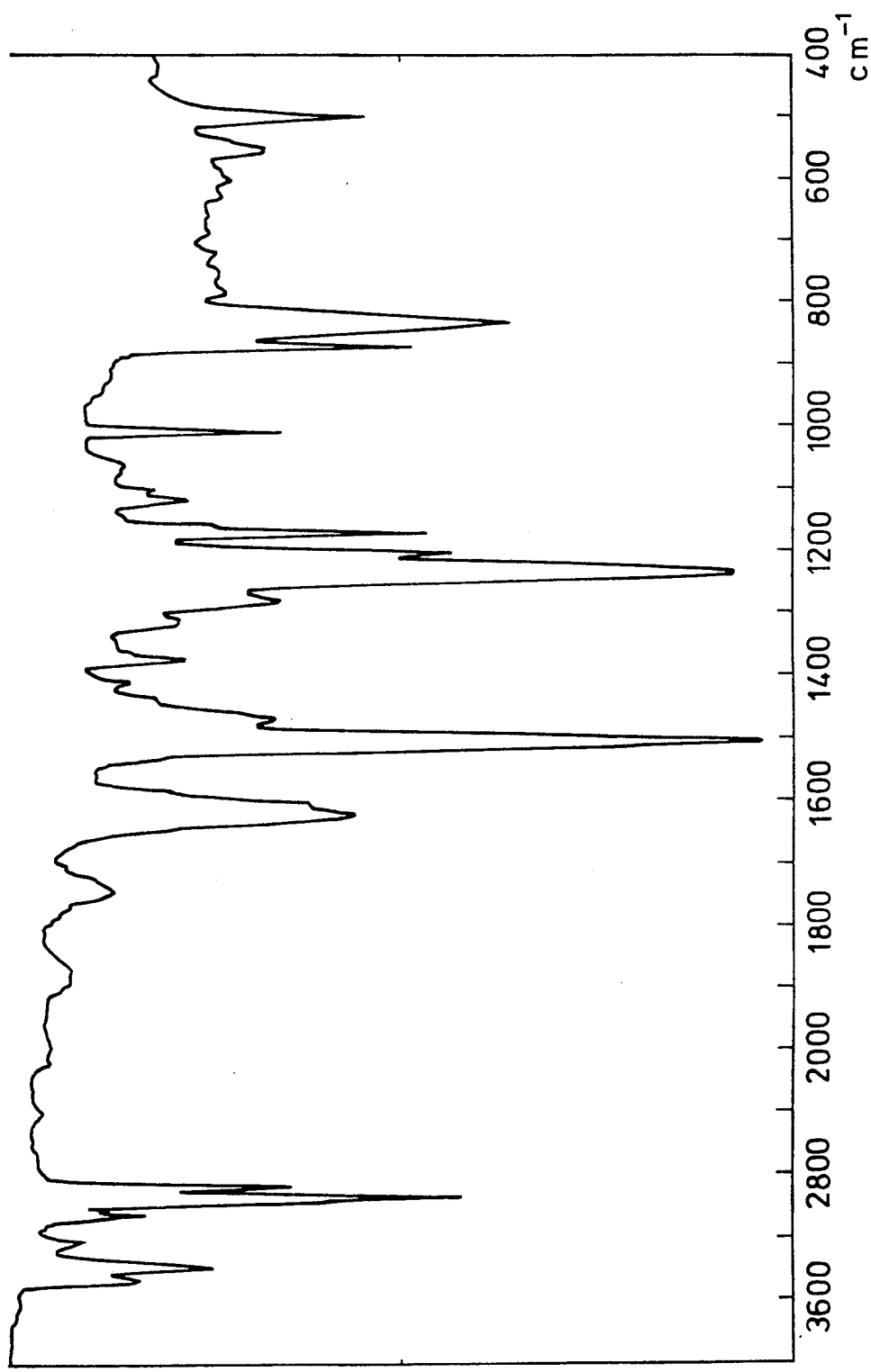
Figure 11:
Figure 12:
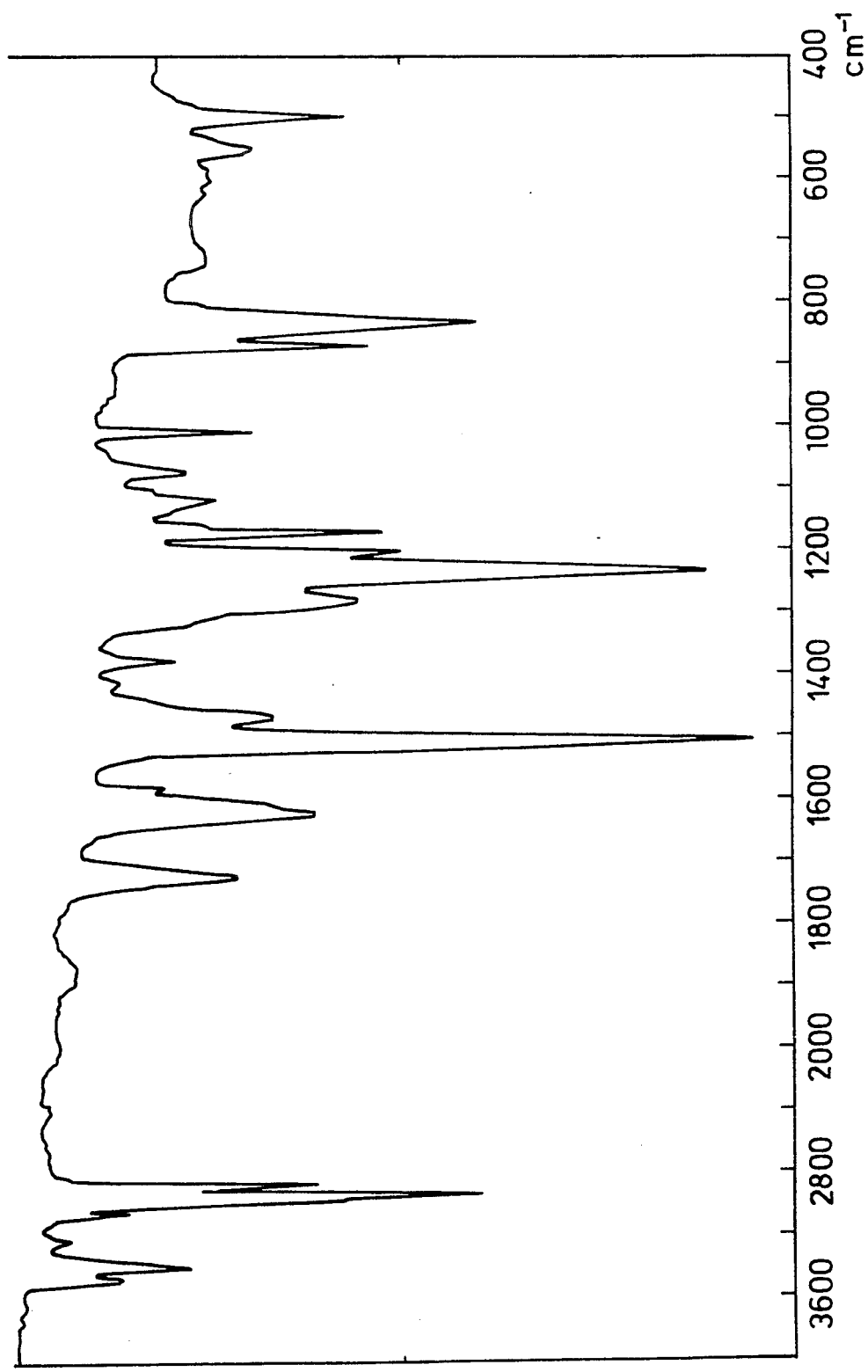
Figure 13:
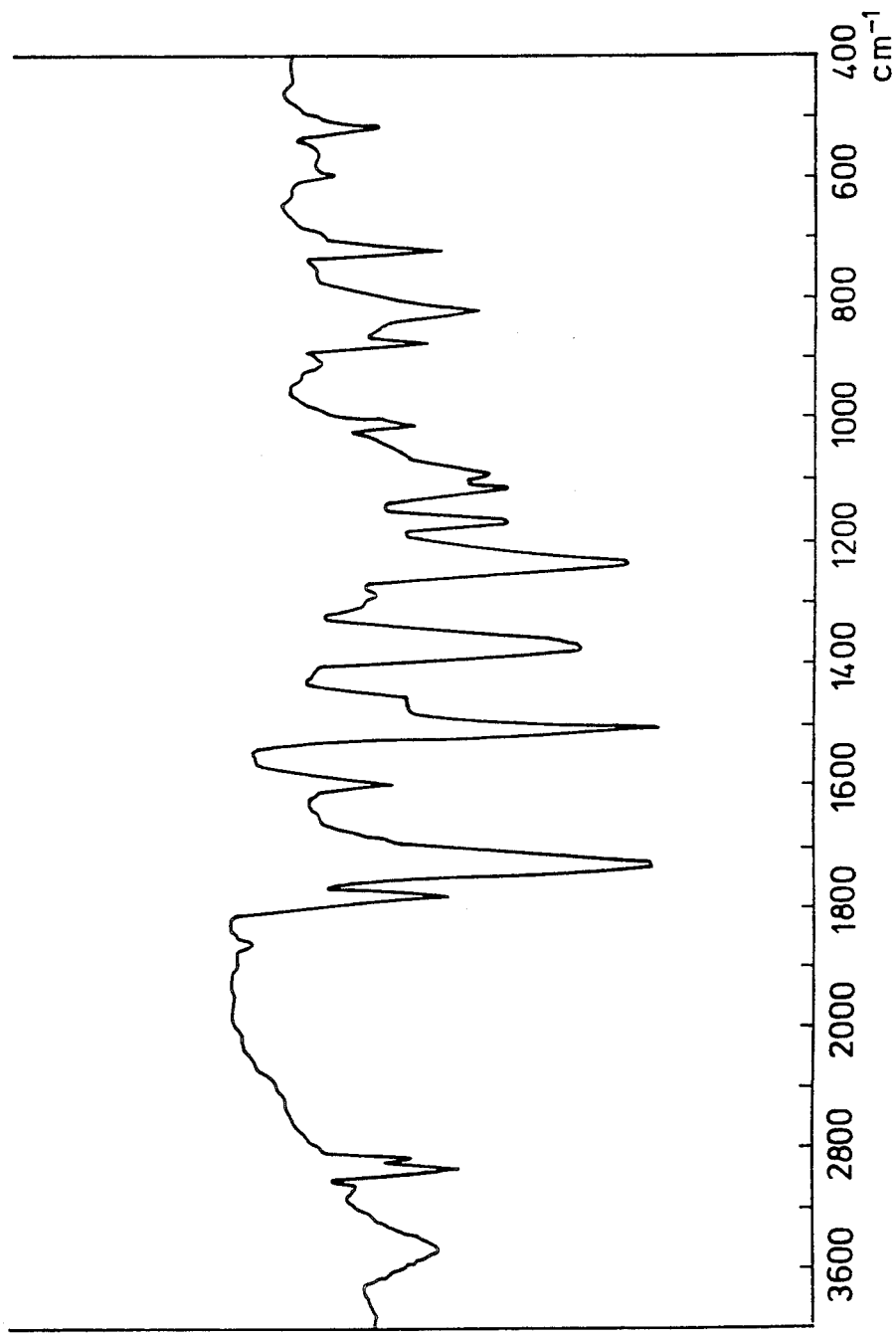
FIGS. 13, 14 and 15 are IR spectra of polyimides which are obtained in Examples 8, 9 and 10, respectively.
Figure 14:
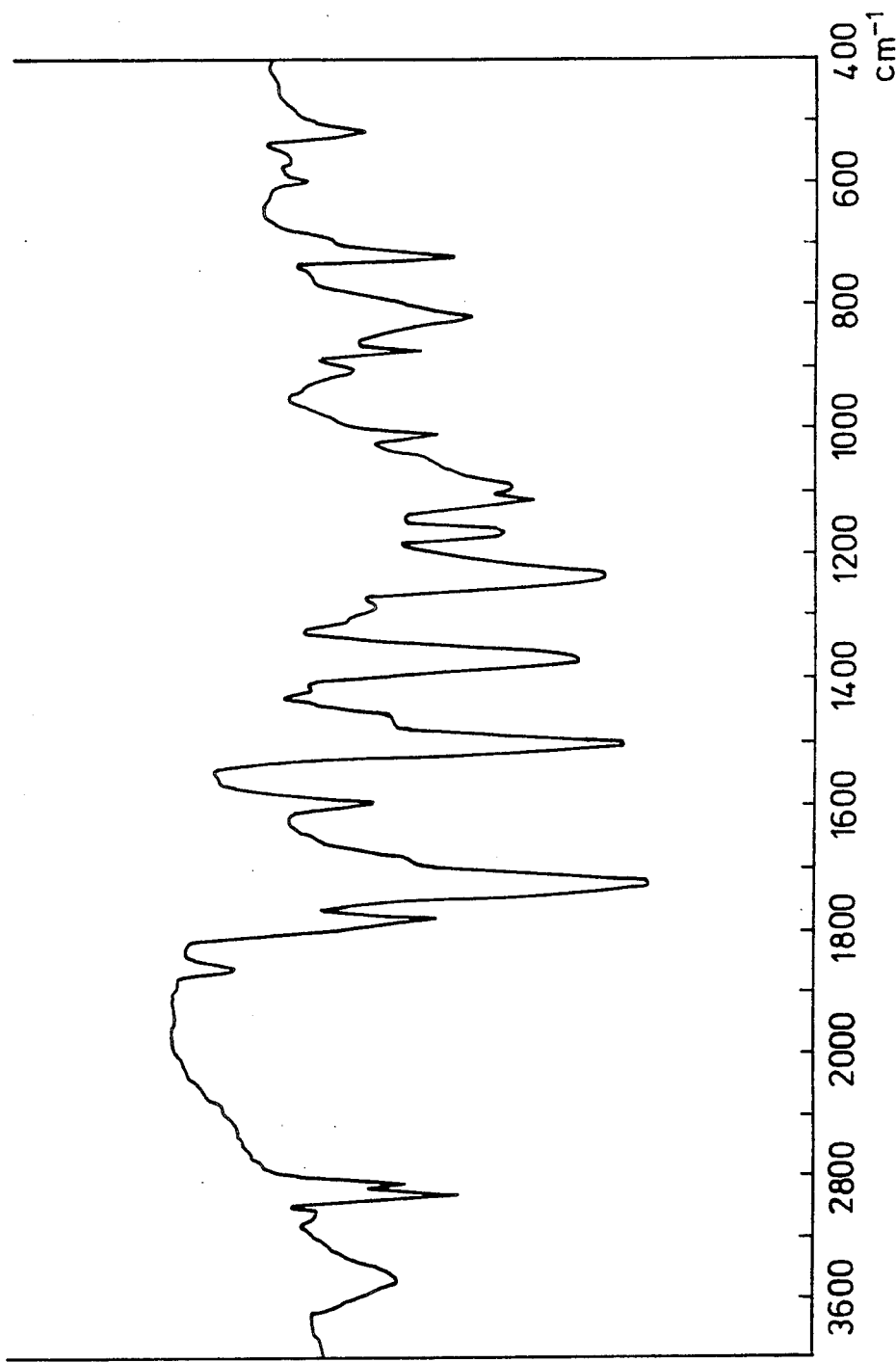
Figure 15:
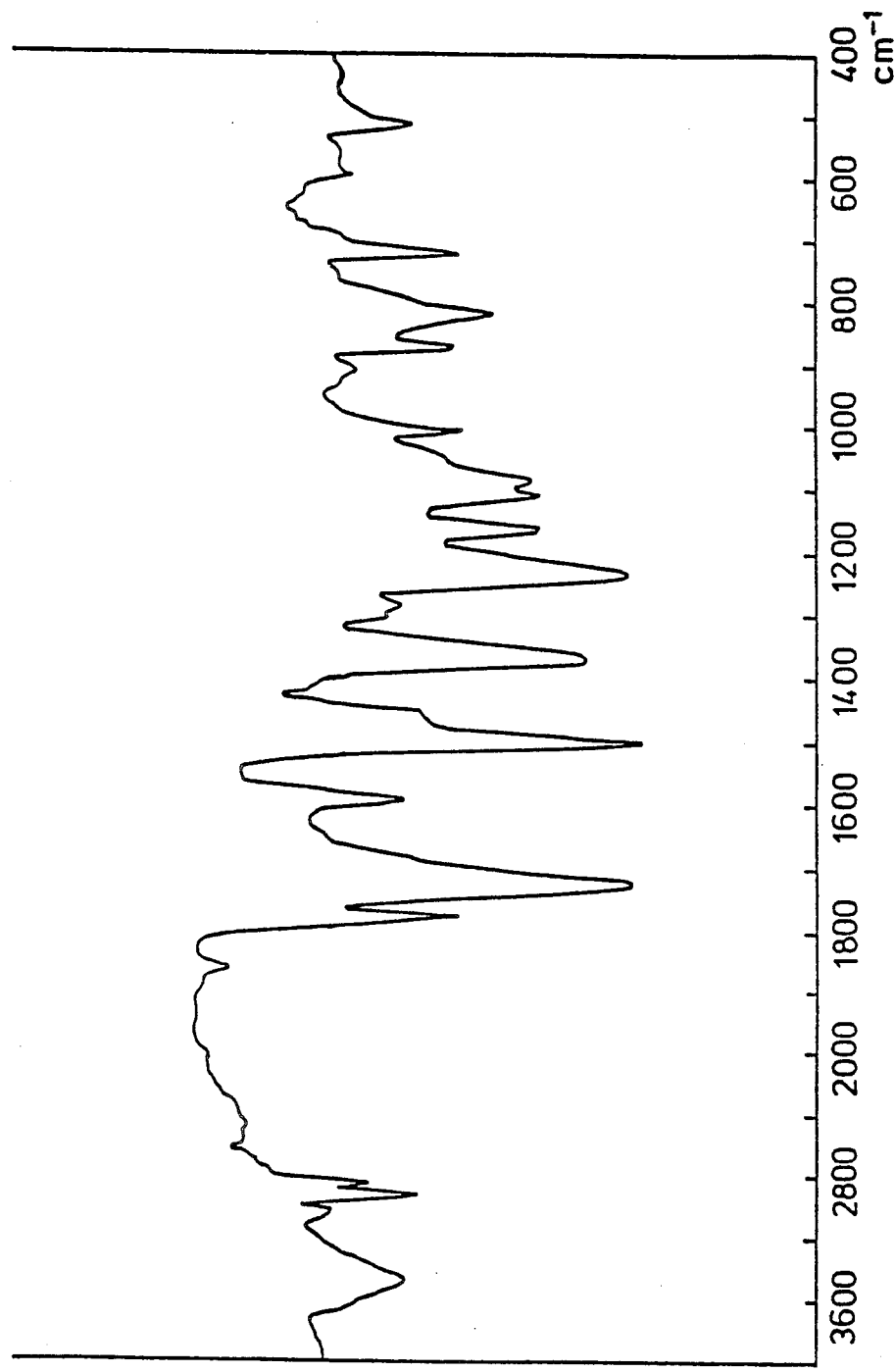

After 2,2-bis(4-hydroxyphenyl)pentane (m.p.: 142.0°–143.9° C.) was given as an intermediate, 2,2-bis[4-(4-nitrophenoxy)phenyl]pentane (m.p.: 151.4°–151.9° C.) was obtained. By the reduction of the obtained compound, 2,2-bis[4-(4-aminophenoxy)phenyl]pentane was obtained. FIGS. 3 and 4 show a NMR spectrum and an IR spectrum of the product, respectively.

EXAMPLES 3–6

Conditions of operation were the same as described in Example 1, except the raw material 2-octanone was changed to corresponding alkanones, respectively, and 2,2-bis[4-(4-aminophenoxy)phenyl]hexane, 2,2-bis[4-(4-aminophenoxy)phenyl]heptane, 2,2-bis[4-(4-aminophenoxy)phenyl]nonane, and 2,2-bis[4-(4-aminophenoxy)phenyl]decane were prepared. The obtained compounds and intermediates, namely, the corresponding diols and dinitro compounds were highly viscous oily substances. The NMR spectra and IR spectra of the obtained diamino compounds were shown in FIGS. 5 and 6, FIGS. 7 and 8, FIGS. 9 and 10, and FIGS. 11 and 12, respectively.

EXAMPLE 7

Using a 100 ml flask equipped with a stirrer, a thermometer, a condenser and a nitrogen displace apparatus, the air in the flask was replaced by nitrogen, and 50 ml of N-methyl-2-pyrrolidone which was previously dehydrated and purified was introduced in the flask. Then, 2.53 g (5.27 mmol) of 2,2-bis[4-(4-aminophenoxy)phenyl]octane prepared in Example 1 was added and dissolved with stirring. The obtained polyamic acid was cooled to 5° C. in an ice bath.

1.15 g (5.27 mmol) of pyromellitic dianhydride was added to the solution at once and reacted with stirring and cooling. After reaction was continued for two hours, a transparent solution containing 6.67% by weight of polyamic acid was obtained. The obtained polyamic acid was consisted of 1:1 by molar ratio of 2,2-bis[4(4-aminophenoxy)phenyl]octane and pyromellitic dianhydride.

The viscosity of the solution was 6.4 centipoises at 25° C. It was determined with a viscometer of E type made by Tokyo Keiki Co. Ltd. at 25°±0.1° C.

The solution was applied by a rotation coating method (spinner method) on transparent glass substrates at 3,000 rpm for ten seconds. Previously, one side of the substrate was coated with transparent conductive coatings (ITO coatings) of indium tin oxide type, and the resultant electrodes were treated with silane coupling agent APS-E made by CHISSO Corporation.

After the application of the solution, the substrates were heated at 200° C. for one hour, and polyimide coatings were obtained.

The thickness of the films that was measured with a feeler type thickness meter was 1,200 Å.

Further, coated surfaces of two substrates were rubbed with a rubbing apparatus for 30 times, respectively. A liquid crystal cell having thickness of 10 μm was assembled by the substrates so as to be oriented in parallel and anti parallel rubbing directions. Liquid crystal composition YY-4006 made by CHISSO Corporation was sealed in the cell. The cell was heated to a temperature of an isotropic liquid, and then cooled.

The aligning properties of the obtained liquid crystal element were excellent. The pretilt angle of the liquid crystal that was measured with the aforementioned measurement method was 19 degrees.

Polyimide films were prepared as described in the above, and the pretilt angles measured by changing the number of times of rubbing are shown in Table 1.

TABLE 1

| Number of times of rubbing | Pretilt angle (degree) |
|---|---|
| 10 | 31 |
| 20 | 24 |
| 30 | 19 |

EXAMPLE 8

Polyimide films were prepared by the following method.

Using a 300 ml flask equipped with a stirrer, a thermometer, a condenser and a nitrogen displace apparatus, the air in the flask was replaced by nitrogen, and 150.71 ml of N-methyl-2-pyrrolidone which was previously dehydrated and purified was introduced in the flask. Then, 5.00 g(10.4 mmol) of 2,2-bis[4-(4-aminophenoxy)phenyl]octane prepared in Example 1 was added and dissolved with stirring. The solution was cooled to 5° C. in an ice bath.

2.60 g(11.9 mmol) of pyromellitic dianhydride was added to the solution at once and reacted with stirring and cooling. The reactant was gradually increased the viscosity and it was exothermic to 10° C. After reaction was continued for one hour, 0.57 g (2.67 mmol) of p-aminophenyl trimethoxysilane was added to the solution, and reacted with stirring at 10° C. for one hour. The obtained transparent solution contained 5% by weight of polyamic acid consisted of 8:7:1.8 by molar ratio of pyromellitic dianhydride, 2,2-bis[4-(4-aminophenoxy)phenyl]octane and p-aminophenyl trimethoxysilane.

The viscosity of the solution was 17.3 centipoises at 25° C. The solution was diluted with Butyl Cellosolve (trade mark) and a solution containing 4.5% of polyamic acid was obtained. The polyamic acid solution was applied by a rotation coating method (spinner method) at 3,000 rpm for 10 seconds on transparent glass substrates on which electrodes of transparent conductive coatings of indium tin oxide type (ITO coatings) were previously set.

After the application of the solution, the substrates were heated at 200° C. for one hour, and polyimide films having thickness of about 1,100 Å were obtained.

Further, using the same method as in Example 7, a liquid crystal element having cell thickness of 10 μm was obtained.

The aligning properties of the obtained liquid crystal element were excellent. The pretilt angle of the liquid crystal that was measured with the aforementioned measurement method was 13 degrees.

EXAMPLE 9

Conditions of operation were the same as described in Example 8, except that 194.61 ml of N-methyl-2-pyrrolidone, 6.60 g (13.0 mmol) of 2,2-bis[4-(4-aminophenoxy)phenyl]decane, 3.24 g(14.9 mmol) of pyromellitic dianhydride and 0.71 g (3.33 mmol) of paminophenyl trimethoxysilane were used. The obtained transparent solution contained 5% by weight of polyamic acid consisted of 8:7:1.8 by molar ratio of pyromellitic dianhydride, 2,2-bis[4-(4-aminophenoxy)phenyl]decane and p-aminophenyl trimethoxysilane.

The viscosity of the solution was 13.5 centipoises at 25° C. The solution was diluted with Butyl Cellosolve and a solution containing 4.5% of polyamic acid was obtained. Using the same method as in Example 7, polyimide type polymer coatings having thickness of about 1,000 Å were prepared, and then a liquid crystal element having cell thickness of 10 μm was obtained. The aligning properties of the obtained element were excellent. The pretilt angle of the element was 18 degrees.

EXAMPLE 10

Conditions of operation were the same as described in Example 8, except that 235.19 ml of N-methyl-2-pyrrolidone, 7.60 g(16.9 mmol) of 2,2-bis[4-(4-aminophenoxy)phenyl]hexane, 4.22 g(19.3 mmol) of pyromellitic dianhydride and 0.93 g (4.36 mmol) of p-aminophenyl trimethoxysilane were used. The obtained transparent solution contained 5% by weight of polyamic acid consisted of 8:7:1.8 by molar ratio of pyromellitic dianhydride, 2,2-bis[4-(4-aminophenoxy)phenyl]hexane and p-aminophenyl trimethoxysilane.

The viscosity of the solution was 38.4 centipoises at 25° C. The solution was diluted with a mixed solution of 1:1 of N-methyl-2-pyrrolidone and Butyl Cellosolve and a solution containing 4.0% of polyamic acid was obtained. Using the same method as in Example 7, polyimide films having thickness of about 1,000 Å were prepared, and then a liquid crystal element having cell thickness of 10 μm was obtained. The aligning properties of the obtained element were excellent. The pretilt angle of the element was seven degrees.

EXAMPLE 11

Conditions of operation were the same as described in Example 8, except that 151.7 ml of N-methyl-2-pyrrolidone, 4.34 g (9.04 mmol) of 2,2-bis[4-(4-aminophenoxy)phenyl]octane, 2.63 g (12.06 mmol) of pyromellitic dianhydride and 1.28 g (6.01 mmol) of p-aminophenyl trimethoxysilane were used. The obtained transparent solution contained 5% by weight of polyamic acid consisted of 8:6:4 by molar ratio of pyromellitic dianhydride, 2,2-bis[4-(4-aminophenoxy)phenyl]octane and p-aminophenyl trimethoxysilane.

The viscosity of the solution was 21 centipoises at 25° C. The solution was diluted with Butyl Cellosolve and a solution containing 4.5% of polyamic acid was obtained. Using the same method as in Example 7, polyimide type polymer coatings having thickness of about 860 Å were prepared, and then a liquid crystal element having cell thickness of 10 μm was obtained. The aligning properties of the obtained element were excellent. The pretilt angle of the element was seven degrees.

COMPARISON EXAMPLE 1

Conditions of operation were the same as described in Example 8, except that 61 ml of N-methyl-2-pyrrolidone, 2.16 g (5.27 mmol) of 2,2-bis[4-(4-aminophenoxy)-phenyl]propane, and 1.15 g (5.27 mmol) of pyromellitic dianhydride were used. The obtained transparent solution contained 5% by weight of polyamic acid that consisted of 1:1 by molar ratio of 2,2-bis[4-(4-aminophenoxy)phenyl]propane and pyromellitic anhydride.

The viscosity of the solution was 203 centipoises at 25° C. The solution was diluted with Butyl Cellosolve and a solution containing 2.5% of polyamic acid was obtained. Using the same method as in Example 7, polyimide films having thickness of about 1000 Å were prepared, and then a liquid crystal element having cell thickness of 10 μm was obtained. The aligning properties of the obtained element were excellent. The pretilt angle of the element was five degrees.

We claim:

1. A liquid crystal aligning film which comprises a polymeric material of a polyimide having a structure unit represented by the formula:

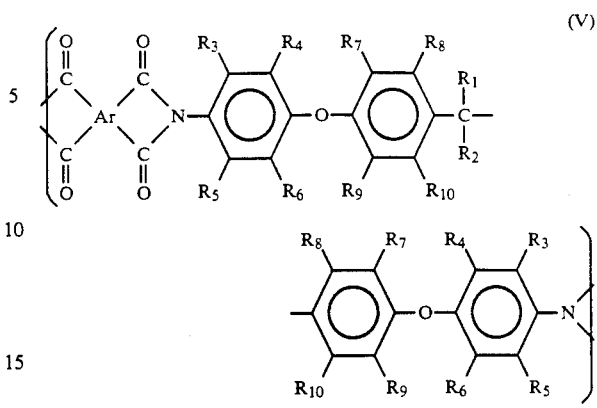

wherein $R_1$ indicates an alkyl group having 3 to 22 carbon atoms, $R_2$ indicates a hydrogen atom or an alkyl group having 1 to 22 carbon atoms, and $R_3$–$R_{10}$ indicate a hydrogen atom or an alkyl group having one to four carbon atoms, respectively, and Ar indicates an aromatic group of four valences.

2. A liquid crystal aligning film as claimed in claim 1, wherein Ar is a benzene-1,2,4,5-tetraakyl group.

3. A liquid crystal aligning film as claimed in claim 1, wherein the polymeric material of the polyimide type makes possible to control a pretilt angle.

4. The liquid crystal aligning film of claim 2, wherein $R_1$ represents an octyl group, $R_2$ represents a methyl group; and $R_3$, $R_4$, $R_5$, $R_6$, $R_7$, $R_8$, $R_9$ and $R_{10}$ each represent a hydrogen atom.

5. The liquid crystal aligning film of claim 2, wherein $R_1$ represents a heptyl group.

6. The liquid crystal aligning film of claim 2, wherein $R_1$ represents a hexyl group.

7. The liquid crystal aligning film of claim 2, wherein $R_1$ represents a pantyl group.

8. The liquid crystal aligning film of claim 2, wherein $R_1$ represents a butyl group.

9. The liquid crystal aligning film of claim 2, wherein $R_1$ represents a propyl group.

* * * * *